United States Patent
Noguchi et al.

(10) Patent No.: US 10,517,850 B2
(45) Date of Patent: *Dec. 31, 2019

(54) COMBINATION OF TAFIA INHIBITOR WITH PLASMINOGEN ACTIVATOR

(71) Applicant: DAIICHI SANKYO COMPANY, LIMITED, Tokyo (JP)

(72) Inventors: Kengo Noguchi, Tokyo (JP); Yusuke Ito, Tokyo (JP); Naoko Edo, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/736,933

(22) PCT Filed: Jun. 16, 2016

(86) PCT No.: PCT/JP2016/067963
§ 371 (c)(1),
(2) Date: Dec. 15, 2017

(87) PCT Pub. No.: WO2016/204239
PCT Pub. Date: Dec. 22, 2016

(65) Prior Publication Data
US 2018/0243268 A1      Aug. 30, 2018

(30) Foreign Application Priority Data

Jun. 17, 2015   (JP) .................................. 2015-121856

(51) Int. Cl.
| | |
|---|---|
| *A61K 31/4172* | (2006.01) |
| *A61P 9/00* | (2006.01) |
| *A61P 39/00* | (2006.01) |
| *A61K 38/48* | (2006.01) |
| *A61K 31/4178* | (2006.01) |
| *A61K 38/49* | (2006.01) |

(52) U.S. Cl.
CPC ...... *A61K 31/4172* (2013.01); *A61K 31/4178* (2013.01); *A61K 38/48* (2013.01); *A61K 38/49* (2013.01); *A61P 9/00* (2018.01); *A61P 39/00* (2018.01)

(58) Field of Classification Search
CPC ............ A61K 31/4172; A61K 31/4178; A61K 38/48; A61K 38/49; A61P 9/00; A61P 39/00
See application file for complete search history.

(56) References Cited

U.S. PATENT DOCUMENTS

| | | | | |
|---|---|---|---|---|
| 8,609,710 B2 * | 12/2013 | Nagata | ................. | C07D 233/64 514/399 |
| 9,340,531 B2 * | 5/2016 | Nagata | ................. | C07D 233/64 |
| 2013/0022587 A1 | 1/2013 | Nagata et al. | | |

FOREIGN PATENT DOCUMENTS

WO   WO 2011/115064 A1   9/2011

OTHER PUBLICATIONS

Oates et al., "Drug therapy: Tissue plasminogen activator", 1988, The New England Journal of Medicine, 319(14), pp. 925-931. (Year: 1988).*
Diana A. Gorog, "Prognostic Value of Plasma Fibrinolysis Activation Markers in Cardiovascular Disease", 2010, JACC, vol. 55, No. 24, pp. 2701-2709. (Year: 2010).*
Okafor et al., "Endogenous Fibrinolysis an Important Mediator of Thrombus Formation and Cardiovascular Risk", 2015, JACC, vol. 65, No. 16, pp. 1683-1699 (Year: 2015).*
Bird et al., "Is exogenous tissue plasminogen activator necessary for antithrombotic efficacy of an inhibitor of thrombin activatable fibrinolysis inhibitor (TAFI) in rats?", *Thrombosis Research*, (2007), 120:549-558.
Islam et al., "3-Mercaptopropionic acids as efficacious inhibitors of activated thrombin activatable fibrinolysis inhibitor (TAFIa)," *Bioorganic & Medicinal Chemistry Letters*, (2007), 17:1349-1354.
Mutch et al., "Thrombus lysis by uPA, scuPA and tPA is regulated by plasma TAFI," *Journal of Thrombosis and Haemostasis*, (2003), 1:2000-2007.
Oshibuchi et al., "Use of rt-Pa (Alteplase) for Acute Cerebral Infarction," *The Journal of Japan Society for Clinical Anesthesia*, (2008), 28(5):807-813, Abstract Only.
Suzuki et al., "Enhancement of Fibrinolysis by EF6265 [(S)-7-Amino-2-[[[(R)-2-methyl-1-(3-phenylpropanoylamino)propyl]hydroxyphosphinoyl]methyl]heptanoic Acid], a Specific Inhibitor of Plasma Carboxypeptidase B," *The Journal of Pharmacology and Experimental Therapeutics*, (2004), 309(2):607-615.
Wang et al., "A novel inhibitor of activated thrombin activatable fibrinolysis inhibitor (TAFIa)—Part II: Enhancement of both exogenous and endogenous fibrinolysis in animal models of thrombosis," *Thromb. Haemost.*, (2007), 97:54-61.
English translation of International Search Report dated Aug. 16, 2016, in PCT Application No. PCT/JP2016/067963, 2 pages.
English translation of Written Opinion dated Aug. 16, 2016, in PCT Application No. PCT/JP2016/067963, 10 pages.
English translation of International Preliminary Report on Patentability dated Dec. 19, 2017, in PCT Application No. PCT/JP2016/067963, 11 pages.

* cited by examiner

*Primary Examiner* — My-Chau T. Tran
(74) *Attorney, Agent, or Firm* — Dorsey & Whitney LLP

(57) ABSTRACT

The present invention provides a pharmaceutical composition for treatment or prevention of thrombosis or embolism or a sequela thereof, comprising a particular TAFIa inhibitor and a plasminogen activator, the TAFIa inhibitor being administered in combination with the plasminogen activator, and a method for treating or preventing thrombosis or embolism or a sequela thereof, comprising administering a particular TAFIa inhibitor in combination with a plasminogen activator to a warm-blooded animal.

35 Claims, 4 Drawing Sheets

| Plasma D-dimer level (µg/mL) | | | | | |
|---|---|---|---|---|---|
| Saline (Control) | Compound A 2.5 µg/kg | t-PA 0.021 mg/kg | t-PA 0.042 mg/kg | t-PA 0.083 mg/kg | Combination |
| 4.4 | 8.6 | 38.4 | 66.0 | 255.2 | 100.6 |
| 3.4 | 13.6 | 16.4 | 46.4 | 205.4 | 180.8 |
| 3.2 | 9.0 | 8.4 | 84.4 | 225.8 | 108.0 |
| 4.8 | 15.6 | 37.6 | 108.6 | 280.2 | 192.8 |
| 2.0 | 8.0 | 20.8 | 108.2 | 285.4 | 137.6 |
| 13.8 | 107.2 | 38.8 | 157.6 | 250.6 | 177.0 |
| 3.2 | 23.0 | 14.4 | 95.4 | 280.0 | 144.2 |

| Plasma D-dimer level (µg/mL) | | | |
| --- | --- | --- | --- |
| Saline (Control) | u-PA (30kU/kg) | Compound A (2.5 µg/kg) | Combination |
| 33.8 | 88.8 | 109.6 | 199.6 |
| 33.6 | 76.0 | 102.6 | 220.2 |
| 11.4 | 81.0 | 99.4 | 214.6 |
| 8.0 | 30.6 | 164.2 | 258.0 |
| 33.8 | 21.4 | 102.8 | 212.4 |
| 17.8 | 41.6 | 170.8 | 206.0 |
| 8.2 | 26.8 | 47.8 | 173.6 |
| 47.2 | 173.8 | 33.4 | 227.4 |

COMBINATION OF TAFIa INHIBITOR WITH PLASMINOGEN ACTIVATOR

This application is a national stage application under 35 U.S.C. § 371 of International Application No. PCT/JP2016/067963, filed Jun. 16, 2016, entitled "COMBINATION OF TAFIa INHIBITOR WITH PLASMINOGEN ACTIVATOR," which claims priority to Japanese Patent Application No. 2015-121856, filed Jun. 17, 2015.

TECHNICAL FIELD

The present invention relates to a pharmaceutical composition for treatment or prevention of thrombosis or embolism or a sequela thereof, comprising a particular TAFIa inhibitor and a plasminogen activator, the TAFIa inhibitor being administered in combination with the plasminogen activator, and a method for treating or preventing thrombosis or embolism or a sequela thereof, comprising administering a particular TAFIa inhibitor in combination with a plasminogen activator to a warm-blooded animal.

BACKGROUND ART

Thrombolytic therapy which involves reopening blood vessels using a plasminogen activator is effective for the treatment of thrombosis or embolism such as acute myocardial infarction, acute-stage cerebral infarction, cardiogenic embolus, or peripheral arterial or venous occlusion. However, this therapy disadvantageously causes adverse reaction such as hemorrhage. In order to avoid this, a sufficient amount of the plasminogen activator may not be able to be administered, and a therapeutic effect may not be exerted due to insufficient lysis of thrombus or embolus. Thus, there is a demand for a treatment method for effectively lysing thrombus or embolus without increasing the dose of the plasminogen activator or by decreasing the dose thereof.

Non Patent Literature 1 and 2 describe an antithrombotic effect brought about by the combined use of a compound that exhibits activated thrombin-activatable fibrinolysis inhibitor (hereinafter, referred to as "TAFIa") inhibitory activity, and a tissue plasminogen activator (hereinafter, referred to as "t-PA").

Patent Literature 1 discloses a compound group that exhibits TAFIa inhibitory activity, and shows that this compound group is useful as a therapeutic drug for thrombosis or embolism. This literature also states that the compound group may be used in combination with an anticoagulant, an antiplatelet drug, or an enzyme related to fibrinolysis, etc.

However, none of this literature describes test results indicating synergistic fibrinolytic activity brought about by the combined use of a particular TAFIa inhibitor and a plasminogen activator, or scientific basis suggesting the test results.

CITATION LIST

Patent Literature

Patent Literature 1: International Publication No. WO 2011/115064

Non Patent Literature

Non Patent Literature 1: Suzuki et al., The Journal of Pharmacology and Experimental Therapeutics, 2004, 309, 607-615

Non Patent Literature 2: Wang et al., Thrombosis and Haemostasis, 2007, 54-61

SUMMARY OF INVENTION

Technical Problem

An object of the present invention is to provide a pharmaceutical composition for treatment or prevention of thrombosis or embolism or a sequela thereof, comprising a particular TAFIa inhibitor and a plasminogen activator, the TAFIa inhibitor being administered in combination with the plasminogen activator, and a method for treating or preventing thrombosis or embolism or a sequela thereof, comprising administering a particular TAFIa inhibitor in combination with a plasminogen activator to a warm-blooded animal.

Solution to Problem

The present inventors have conducted studies with the aim of investigating an effect brought about by the combined use of a TAFIa inhibitor and a plasminogen activator. As a result, the present inventors have found that synergistic fibrinolytic activity is exerted by administering a particular TAFIa inhibitor in combination with a plasminogen activator.

Specifically, the present invention encompasses the following aspects.

(1) A pharmaceutical composition for treatment or prevention of thrombosis or embolism or a sequela thereof, comprising a compound represented by the formula (I):

[Formula 1]

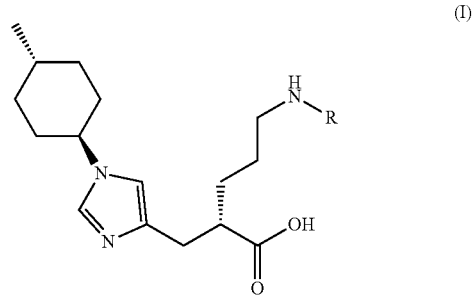

wherein R represents a hydrogen atom, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a {1-[(cyclohexylcarbonyl)oxy]ethoxy}carbonyl group, or a (1-acetoxyethoxy)carbonyl group or a pharmacologically acceptable salt thereof and a plasminogen activator, the compound or the pharmacologically acceptable salt thereof being administered in combination with the plasminogen activator, wherein the pharmaceutical composition exhibits synergistic fibrinolytic activity.

(2) The pharmaceutical composition according to (1), wherein the fibrinolytic activity is calculated from a D-dimer level in plasma.

(3) The pharmaceutical composition according to (1) or (2), wherein the compound represented by the formula (I) or the pharmacologically acceptable salt thereof and the plasminogen activator are contained as active ingredients in separate preparations, respectively, and administered at the same time or different times.

(4) The pharmaceutical composition according to (1) or (2), wherein both the compound represented by the formula (I) or the pharmacologically acceptable salt thereof and the plasminogen activator are contained and administered as active ingredients in a single preparation.

(5) The pharmaceutical composition according to any one of (1) to (4), wherein the plasminogen activator is a tissue plasminogen activator (t-PA).

(6) The pharmaceutical composition according to (5), wherein the t-PA is alteplase.

(7) The pharmaceutical composition according to any one of (1) to (4), wherein the plasminogen activator is urokinase (u-PA).

(8) The pharmaceutical composition according to any one of (1) to (7), wherein R is a hydrogen atom.

(9) The pharmaceutical composition according to (8), wherein the pharmacologically acceptable salt is a p-toluenesulfonate.

(10) The pharmaceutical composition according to any one of (1) to (7), wherein R is a [1-(isobutyryloxy)ethoxy] carbonyl group.

(11) The pharmaceutical composition according to (10), wherein R is a [(1R)-1-(isobutyryloxy)ethoxy]carbonyl group.

(12) The pharmaceutical composition according to any one of (1) to (11), wherein the thrombosis or embolism is acute coronary syndrome; venous thromboembolism; thrombosis or embolism occurring in the cardiovascular system after a surgical operation; thrombosis or embolism after an artificial joint replacement operation; inflammation-related intravascular disease; peripheral vascular disorder-derived or -related disease; tumor-related disease; or organ disorder attributed to thrombus or embolus.

(13) The pharmaceutical composition according to (12), wherein the thrombosis or embolism is myocardial infarction, stable angina, or unstable angina; deep vein thrombosis or pulmonary embolism; thrombosis or embolism occurring in the cardiovascular system after vessel revascularization, angioplasty, stent placement, or bypass surgery; thrombosis or embolism after a knee joint replacement operation or hip joint replacement operation; intravascular disease related to sepsis or disseminated intravascular coagulation syndrome (DIC); disease derived from or related to peripheral arterial occlusion (PAO), arteriosclerosis, or diabetes mellitus; disease related to solid cancer or blood cancer; or organ disorder attributed to pulmonary embolus, cerebral infarction, or renal infarction.

(14) The pharmaceutical composition according to any one of (1) to (11), wherein the thrombosis or embolism is disease caused by contact with foreign matter in the body; or disease caused by contact between blood and a medical device outside the body.

(15) The pharmaceutical composition according to (14), wherein the thrombosis or embolism is disease caused by contact with a medical device.

(16) The pharmaceutical composition according to (15), wherein the thrombosis or embolism is disease caused by contact with a joint prosthesis used in joint replacement, a vascular catheter, a vascular prosthesis, an intravascular stent, or a prosthetic valve.

(17) The pharmaceutical composition according to (14), wherein the thrombosis or embolism is disease caused by contact between blood and a pump oxygenator used in a cardiac operation or a medical device used in hemodialysis.

(18) The pharmaceutical composition according to any one of (1) to (11), wherein the thrombosis or embolism is myocardial infarction, angina pectoris, acute coronary syndrome, cerebral infarction, deep vein thrombosis, pulmonary embolism, or peripheral arterial occlusion.

(19) A method for treating or preventing thrombosis or embolism or a sequela thereof, comprising administering a compound represented by the formula (I):

[Formula 2]

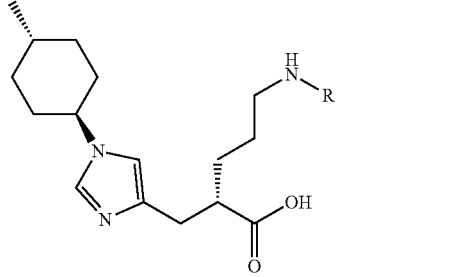

wherein R represents a hydrogen atom, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a {1-[(cyclohexylcarbonyl)oxy]ethoxy}carbonyl group, or a (1-acetoxyethoxy)carbonyl group or a pharmacologically acceptable salt thereof in combination with a plasminogen activator to a warm-blooded animal, wherein the method exhibits synergistic fibrinolytic activity.

(20) The method according to (19), wherein the fibrinolytic activity is calculated from a D-dimer level in plasma.

(21) The method according to (19) or (20), wherein the compound represented by the formula (I) or the pharmacologically acceptable salt thereof and the plasminogen activator are contained as active ingredients in separate preparations, respectively, and administered at the same time or different times.

(22) The method according to (19) or (20), wherein both the compound represented by the formula (I) or the pharmacologically acceptable salt thereof and the plasminogen activator are contained and administered as active ingredients in a single preparation.

(23) The method according to any one of (19) to (22), wherein the plasminogen activator is a tissue plasminogen activator (t-PA).

(24) The method according to (23), wherein the t-PA is alteplase.

(25) The method according to any one of (19) to (22), wherein the plasminogen activator is urokinase (u-PA).

(26) The method according to any one of (19) to (25), wherein R is a hydrogen atom.

(27) The method according to (26), wherein the pharmacologically acceptable salt is a p-toluenesulfonate.

(28) The method according to any one of (19) to (25), wherein R is a [1-(isobutyryloxy)ethoxy]carbonyl group.

(29) The method according to (28), wherein R is a [(1R)-1-(isobutyryloxy)ethoxy]carbonyl group.

(30) The method according to any one of (19) to (29), wherein the thrombosis or embolism is acute coronary syndrome; venous thromboembolism; thrombosis or embolism occurring in the cardiovascular system after a surgical operation; thrombosis or embolism after an artificial joint replacement operation; inflammation-related intravascular disease; peripheral vascular disorder-derived or -related disease; tumor-related disease; or organ disorder attributed to thrombus or embolus.

(31) The method according to (30), wherein the thrombosis or embolism is myocardial infarction, stable angina, or unstable angina; deep vein thrombosis or pulmonary embolism; thrombosis or embolism occurring in the cardiovascular system after vessel revascularization, angioplasty, stent placement, or bypass surgery; thrombosis or embolism after a knee joint replacement operation or hip joint replacement operation; intravascular disease related to sepsis or disseminated intravascular coagulation syndrome (DIC); disease derived from or related to peripheral arterial occlusion (PAO), arteriosclerosis, or diabetes mellitus; disease related to solid cancer or blood cancer; or organ disorder attributed to pulmonary embolus, cerebral infarction, or renal infarction.

(32) The method according to any one of (19) to (29), wherein the thrombosis or embolism is disease caused by contact with foreign matter in the body; or disease caused by contact between blood and a medical device outside the body.

(33) The method according to (32), wherein the thrombosis or embolism is disease caused by contact with a medical device.

(34) The method according to (33), wherein the thrombosis or embolism is disease caused by contact with a joint prosthesis used in joint replacement, a vascular catheter, a vascular prosthesis, an intravascular stent, or a prosthetic valve.

(35) The method according to (32), wherein the thrombosis or embolism is disease caused by contact between blood and a pump oxygenator used in a cardiac operation or a medical device used in hemodialysis.

(36) The method according to any one of (19) to (29), wherein the thrombosis or embolism is myocardial infarction, angina pectoris, acute coronary syndrome, cerebral infarction, deep vein thrombosis, pulmonary embolism, or peripheral arterial occlusion.

(37) The method according to any one of (19) to (36), wherein the warm-blooded animal is a human.

Advantageous Effects of Invention

The present invention can provide a pharmaceutical composition for treatment or prevention of thrombosis or embolism or a sequela thereof, comprising a particular TAFIa inhibitor and a plasminogen activator, the TAFIa inhibitor being administered in combination with the plasminogen activator, and a method for treating or preventing thrombosis or embolism or a sequela thereof, comprising administering a particular TAFIa inhibitor in combination with a plasminogen activator to a warm-blooded animal.

DESCRIPTION OF EMBODIMENTS

Figures 1, 2:
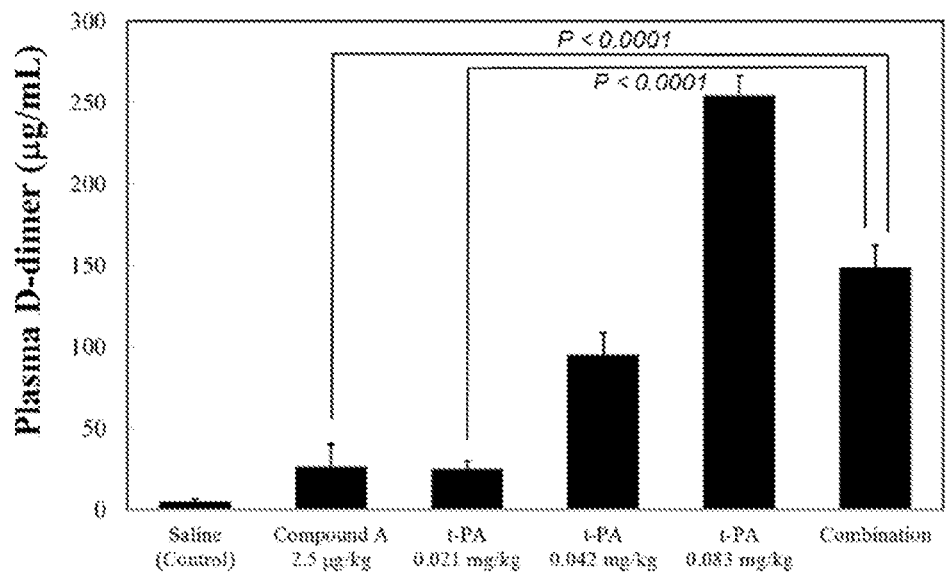
FIG. 1 is a diagram showing fibrinolytic activity (D-dimer level) in 7 cases each of a control (saline) group, a compound A (2.5 µg/kg) group, t-PA (0.083, 0.042, and 0.021 mg/kg) groups, and a combination group of compound A (2.5 µg/kg) and t-PA (0.021 mg/kg).
FIG. 2 is a diagram showing a mean (standard error) of fibrinolytic activity (D-dimer level) in 7 cases each of a control (saline) group, a compound A (2.5 µg/kg) group, t-PA (0.083, 0.042, and 0.021 mg/kg) groups, and a combination group of compound A (2.5 µg/kg) and t-PA (0.021 mg/kg), and the comparison (P value) of the compound A (2.5 µg/kg) and t-PA (0.021 mg/kg) single administration groups with the combination group.

The compound represented by the formula (I):

[Formula 3]

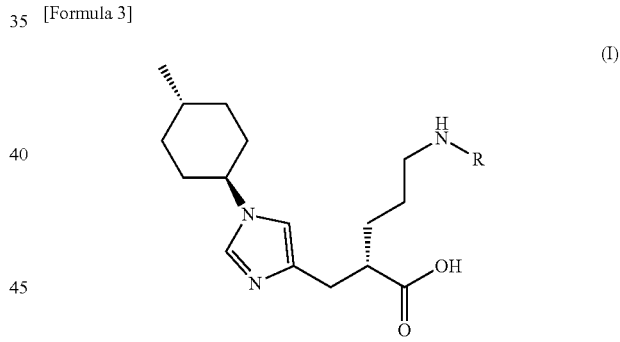

(I)

used in the present invention can be produced by a method described in the pamphlet of International Publication No. WO 2011/115064 or a method equivalent thereto.

A compound represented by the formula (I) wherein R is a hydrogen atom, i.e., (2S)-5-amino-2-{[1-(trans-4-methylcyclohexyl)-1H-imidazol-4-yl]methyl}valeric acid, is a compound that exhibits TAFIa inhibitory activity. The compound is described in Example 15 (2S form) in the pamphlet of International Publication No. WO 2011/115064.

A compound represented by the formula (I) wherein R is a [(5-methyl-2-oxo-1,3-dioxol-4-yl)methoxy]carbonyl group, a [1-(isobutyryloxy)ethoxy]carbonyl group, [1-(2,2-dimethylpropanoyloxy)ethoxy]carbonyl group, a {1-[(cyclohexylcarbonyl)oxy]ethoxy}carbonyl group, a (1-acetoxyethoxy)carbonyl group, or a [(1R)-1-(isobutyryloxy)ethoxy]carbonyl group, i.e., (2S)-2-{[1-(trans-4-methylcyclohexyl)-1H-imidazol-4-yl]methyl}-5-({[(5-methyl-2-oxo-1,3-dioxol-4-yl)methoxy]carbonyl}amino) valeric acid, (2S)-5-({[1-(isobutyryloxy)ethoxy]

carbonyl}amino)-2-{[1-(trans-4-methylcyclohexyl)-1H-imidazol-4-yl]methyl}valeric acid, (2S)-5-({[1-(2,2-dimethylpropanoyloxy)ethoxy]carbonyl}amino)-2-{[1-(trans-4-methylcyclohexyl)-1H-imidazol-4-yl]methyl}valeric acid, (2S)-5-[({1-[(cyclohexylcarbonyl)oxy]ethoxy}carbonyl)amino]-2-{[1-(trans-4-methylcyclohexyl)-1H-imidazol-4-yl]methyl}valeric acid, (2S)-5-{[(1-acetoxyethoxy)carbonyl]amino}-2-{[1-(trans-4-methylcyclohexyl)-1H-imidazol-4-yl]methyl}valeric acid, or (2S)-5-({[(1R)-1-(isobutyryloxy)ethoxy]carbonyl}amino)-2-{[1-(trans-4-methylcyclohexyl)-1H-imidazol-4-yl]methyl}valeric acid is a prodrug that is converted to (2S)-5-amino-2-{[1-(trans-4-methylcyclohexyl)-1H-imidazol-4-yl]methyl}valeric acid serving as an active ingredient through reaction with an enzyme, gastric acid, or the like in vivo. The compounds are described in Examples 19, 20, 22, 23, 27, and 32 in the pamphlet of International Publication No. WO 2011/115064.

Examples of an acid-addition salt with an acid as the pharmacologically acceptable salt of the compound represented by the formula (I) can include: hydrohalides such as hydrofluoride, hydrochloride, hydrobromide, and hydroiodide; inorganic acid salts such as nitrate, perchlorate, sulfate, and phosphate; lower alkanesulfonates such as methanesulfonate, trifluoromethanesulfonate, and ethanesulfonate; arylsulfonates such as benzenesulfonate and p-toluenesulfonate; organic acid salts such as acetate, malate, fumarate, succinate, citrate, tartrate, oxalate, and maleate; and amino acid salts such as ornitate, glutamate, and aspartate.

When R in the compound represented by the formula (I) is a hydrogen atom, the pharmacologically acceptable salt is preferably a hydrohalide or an arylsulfonate, more preferably hydrochloride, benzenesulfonate, or p-toluenesulfonate, even more preferably benzenesulfonate or p-toluenesulfonate, particularly preferably p-toluenesulfonate.

(2S)-5-Amino-2-{[1-(trans-4-methylcyclohexyl)-1H-imidazol-4-yl]methyl}valeric acid p-toluenesulfonate anhydrate is described in Example 40 in the pamphlet of International Publication No. WO 2011/115064.

Examples of a base-addition salt with a base can include: alkali metal salts such as sodium salts, potassium salts, and lithium salts; alkaline-earth metal salts such as calcium salts and magnesium salts; inorganic salts such as ammonium salts; organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts; and amino acid salts such as arginine salts.

The compound represented by the formula (I) or the pharmacologically acceptable salt thereof may be present in a solvate form. These solvates are also encompassed in the compound used in the present invention or the salt thereof. The solvate is not particularly limited as long as it is pharmacologically acceptable. Specifically, hydrates, ethanolates, or the like are preferable, and hydrates are more preferable.

The plasminogen activator defined in the present invention includes both of t-PA and urokinase (hereinafter, referred to as "u-PA").

The t-PA also includes a recombinant tissue plasminogen activator (hereinafter, referred to as "rt-PA").

Examples of the rt-PA include alteplase having the same amino acid sequence as that of naturally occurring t-PA, and monteplase, pamiteplase, and nateplase having a partial amino acid substitution in order to prolong half-life. All of them are included in the t-PA defined in the present invention.

In the present invention, the phrase "administered in combination" includes the case where the compound represented by the formula (I) or the pharmacologically acceptable salt thereof and the plasminogen activator are contained as active ingredients in separate preparations, respectively, and administered at the same time or different times, and the case where the compound represented by the formula (I) or the pharmacologically acceptable salt thereof and the plasminogen activator are contained and administered as active ingredients in a single preparation.

The compound represented by the formula (I) or the pharmacologically acceptable salt thereof may be an oral preparation or may be a parenteral preparation.

Examples of the oral preparation include tablets, pills, powders, granules, capsules, solutions, suspensions, emulsions, syrups, and elixirs. These forms of pharmaceutical drugs are usually prepared as a pharmaceutical composition containing the compound represented by the general formula (I) or the salt thereof as a principal ingredient mixed with pharmaceutically acceptable additives such as diluents, excipients, or carriers. In addition to this, the preparation of the pharmaceutical composition can be performed according to a conventional method using one or more appropriately selected according to need from any appropriate pharmaceutically acceptable binders, disintegrants, lubricants, swelling agents, swelling aids, coating agents, plasticizers, stabilizers, antiseptics, antioxidants, coloring agents, solubilizing agents, suspending agents, emulsifying agents, sweeteners, preservatives, buffers, humectants, and so on.

Examples of the parenteral preparation include injections, ointments, gels, creams, poultice, patches, aerosols, inhalants, sprays, eye drops, nasal drops, and suppositories. These forms of pharmaceutical drugs are usually prepared as a pharmaceutical composition containing the compound represented by the formula (I) or the salt thereof as a principal ingredient mixed with pharmaceutically acceptable additives such as diluents, excipients, or carriers. In addition to this, the preparation of the pharmaceutical composition can be performed according to a conventional method using one or more appropriately selected according to need from any appropriate pharmaceutically acceptable stabilizers, antiseptics, solubilizing agents, humectants, preservatives, antioxidants, flavors, gelling agents, neutralizing agents, buffers, tonicity agents, surfactants, coloring agents, thickeners, wetting agents, fillers, absorption promoters, suspending agents, binders, and so on.

The plasminogen activator is used as an injection. Thus, in the case of using the compound represented by the formula (I) or the pharmacologically acceptable salt thereof as an injection, the compound represented by the formula (I) or the pharmacologically acceptable salt thereof and the plasminogen activator can be contained and administered as active ingredients in a single preparation. On the other hand, in the case of using the compound represented by the formula (I) or the pharmacologically acceptable salt thereof as a preparation other than an injection, the compound represented by the formula (I) or the pharmacologically acceptable salt thereof and the plasminogen activator are contained as active ingredients in separate preparations, respectively, and administered at the same time or different times.

The single dose of the compound represented by the formula (I) is 0.01 to 5000 mg, preferably 0.1 to 1000 mg, more preferably 1 to 200 mg.

The single standard dose of t-PA used alone is 290,000 to 435,000 I.U./kg for alteplase, 300,000 I.U./kg for nateplase, 275,000 I.U./kg for monteplase, and 65,000 I.U./kg for pamiteplase. The single standard dose of u-PA used alone is 60,000 to 240,000 U/day.

However, the dose of the plasminogen activator can be reduced by combined use with the compound represented by the formula (I).

Also, thrombus or embolus can be lysed more effectively by the combined use of the compound represented by the formula (I) with the standard dose of the plasminogen activator than by single administration of the plasminogen activator.

In the present invention, the fibrinolytic activity can be calculated by a method known in the art, for example, by measuring a D-dimer level in plasma.

In the present invention, the phrase "exhibits synergistic fibrinolytic activity" means that fibrinolytic activity significantly better than the total fibrinolytic activity brought about by the two components each administered alone is exerted. Whether "exhibits synergistic fibrinolytic activity" applies can be confirmed by two-way ANOVA.

The pharmaceutical composition and the method of the present invention can be used in the treatment or prevention of thrombosis or embolism or a sequela thereof.

Specific examples of the "thrombosis or embolism" can include: acute coronary syndrome; venous thromboembolism; thrombosis or embolism occurring in the cardiovascular system after a surgical operation; thrombosis or embolism after an artificial joint replacement operation; inflammation-related intravascular disease; peripheral vascular disorder-derived or -related disease; tumor-related disease; and organ disorder attributed to thrombus or embolus. More specific examples thereof can include: myocardial infarction, stable angina, and unstable angina; deep vein thrombosis and pulmonary embolism; thrombosis or embolism occurring in the cardiovascular system after vessel revascularization, angioplasty, stent placement, or bypass surgery; thrombosis or embolism after a knee joint replacement operation or hip joint replacement operation; intravascular disease related to sepsis or disseminated intravascular coagulation syndrome (DIC); disease derived from or related to peripheral arterial occlusion (PAO), arteriosclerosis, or diabetes mellitus; disease related to solid cancer or blood cancer; and organ disorder attributed to pulmonary embolus, cerebral infarction, or renal infarction.

Other specific examples of the "thrombosis or embolism" can include: disease caused by contact with foreign matter in the body; and, disease caused by contact between blood and a medical device outside the body. More specific examples thereof can include: disease caused by contact with a medical device; and disease caused by contact between blood and a pump oxygenator used in a cardiac operation or a medical device used in hemodialysis. Further specific examples thereof can include disease caused by contact with a joint prosthesis used in joint replacement, a vascular catheter, a vascular prosthesis, an intravascular stent, or a prosthetic valve.

More preferable specific examples of the "thrombosis or embolism" can include myocardial infarction, angina pectoris, acute coronary syndrome, cerebral infarction, deep vein thrombosis, pulmonary embolism, and peripheral arterial occlusion.

The method of the present invention can be used for a warm-blooded animal (particularly, human).

EXAMPLES

Hereinafter, the present invention will be described specifically with reference to Examples. However, the present invention is not limited to these methods by any means.

Example 1

Test on Combined Use with t-PA
1. Preparation of Administration Solution
(1) (2S)-5-Amino-2-{[1-(trans-4-methylcyclohexyl)-1H-imidazol-4-yl]methyl}valeric acid p-toluenesulfonate anhydrate (hereinafter, referred to as "compound A") was dissolved in saline to prepare a 1.0 mg/mL solution. The solution was further diluted to 0.0050 mg/mL using saline. The dose of compound A was indicated in terms of a free form (conversion factor: 0.6301).
(2) t-PA (alteplase (Activacin (registered trademark) for Injection 6,000,000), Kyowa Hakko Kirin Co., Ltd.) was adjusted to 600,000 I.U./mL (which was defined as 1.0 mg/mL) with injectable water included therein. The resulting solution was further diluted to 0.17, 0.083, and 0.042 mg/mL using saline.
(3) The 0.0050 mg/mL compound A solution was mixed with an equal amount of saline or the 0.042 mg/mL t-PA solution to respectively prepare administration solutions for a compound A (2.5 µg/kg) group and a combination group. The 0.17, 0.083, and 0.042 mg/mL t-PA solutions were mixed with an equal amount of saline to respectively prepare administration solutions for t-PA (0.083, 0.042, and 0.021 mg/kg) groups.
(4) 4 mL of saline was added to 10 mL (standard) of a tissue factor (Dade (registered trademark) Innovin (registered trademark), Sysmex Corp.) to prepare a tissue factor solution.
2. Administration to Rat and Measurement of Fibrinolytic Activity
(1) Ten-week-old male Wistar rats (Japan SLC, Inc.) were fasted from a day before the experiment. On the basis of their body weights measured in the morning on the day of the experiment, 7 rats were assigned to each of 6 groups: a control (saline) group, a compound A (2.5 µg/kg) group, t-PA (0.021, 0.042, and 0.083 mg/kg) groups, and a combination group of compound A (2.5 µg/kg) and t-PA (0.021 mg/kg).
(2) These rats were anesthetized by the administration of 100 mg/kg thiopental sodium (Ravonal (registered trademark), Mitsubishi Tanabe Pharma Corp.), and the tissue factor solution was continuously administered at 7.5 mL/kg/hr for 20 minutes from the jugular veins. 25 minutes after the start of the administration of the tissue factor, the administration solution for each group was rapidly administered from the jugular veins. 45 minutes after the start of the administration of the tissue factor, blood was collected from the jugular veins into syringes supplemented with citric acid in advance, and plasma was prepared by centrifugation. The plasma was diluted 20-fold using a factor diluent (LSI Medience Corp.). D-dimer levels were measured using LPIA-Ace D-D dimer II and ACL TOP 500 CTS (Instrumentation Laboratory) and used as an index for fibrinolytic activity (FIG. 1).
3. Statistical Analysis
(1) Microsoft Excel 2003 and SAS System Release 8.2 were used in statistical analysis.
(2) For each group, the basic statistics (mean and standard error) of the D-dimer levels were calculated and used as results relating to fibrinolytic activity (Table 1).

TABLE 1

| Group | N | D-dimer level (μg/mL) | |
| --- | --- | --- | --- |
| | | Mean | Standard error |
| Control (saline) group | 7 | 5.0 | 1.5 |
| Compound A (2.5 μg/kg) group | 7 | 26.4 | 13.6 |
| t-PA (0.021 mg/kg) group | 7 | 25.0 | 4.9 |
| t-PA (0.042 mg/kg) group | 7 | 95.2 | 13.4 |
| t-PA (0.083 mg/kg) group | 7 | 254.7 | 11.5 |
| Combination group of compound A (2.5 μg/kg) and t-PA (0.021 mg/kg) | 7 | 148.7 | 13.7 |

(3) The comparison of the compound A (2.5 μg/kg) group with the control (saline) group was carried out by the Student's t test. The calculated P value was rounded off and indicated down to four decimal places, and the significance level was set to two-sided 5%. As a result, the compound A (2.5 μg/kg) group did not exhibit significantly excellent fibrinolytic activity (D-dimer level) with respect to the control (saline) group (P=0.1431).

(4) The comparison of the t-PA (0.021, 0.042, and 0.083 mg/kg) groups with the control (saline) group was carried out by the parametric Dunnett's test. The calculated P value was rounded off and indicated down to four decimal places, and the significance level was set to two-sided 5%.

As a result, the t-PA (0.021 mg/kg) group did not exhibit significantly excellent fibrinolytic activity (D-dimer level) with respect to the control (saline) group (P=0.3080).

On the other hand, the t-PA (0.042 and 0.083 mg/kg) groups exhibited significantly excellent fibrinolytic activity (D-dimer level) with respect to the control (saline) group (P<0.0001).

(5) The comparison of the compound A (2.5 μg/kg) group or the t-PA (0.021 mg/kg) single administration group with the combination group was carried out by the parametric Dunnett's test. The calculated P value was rounded off and indicated down to four decimal places, and the significance level was set to two-sided 5%. As a result, the combination group exhibited significantly excellent fibrinolytic activity (D-dimer level) with respect to both of the single administration groups (P<0.0001) (FIG. 2).

Figures 3, 4:
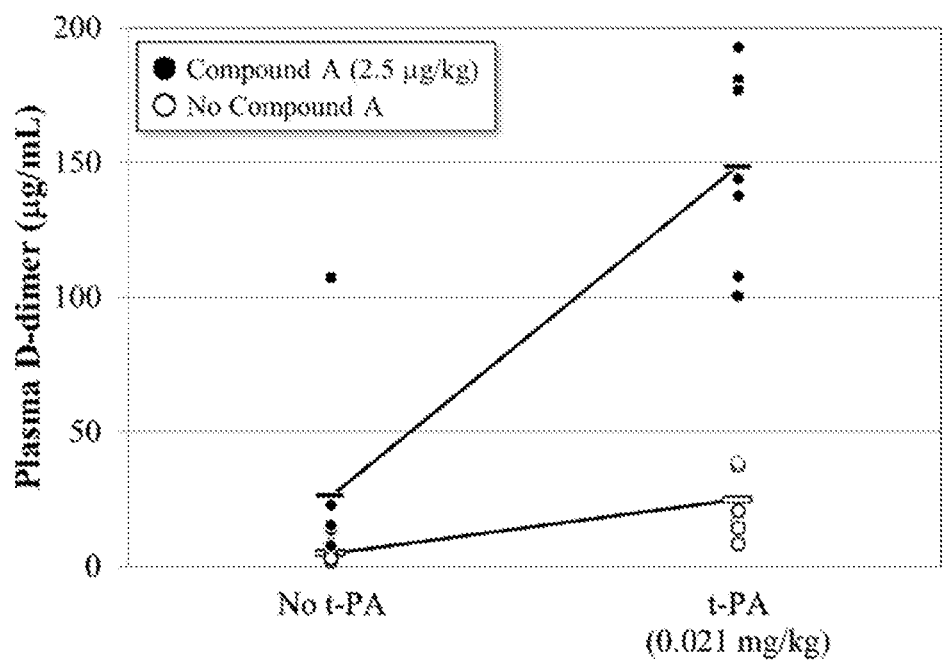
FIG. 3 is a diagram showing the comparison of the compound A (2.5 µg/kg) and t-PA (0.021 mg/kg) single administration groups with the combination group by two-way ANOVA. In the diagram, the plot depicts individual values, and the horizontal lines depict a mean of 7 cases each of the groups.
FIG. 4 is a diagram showing fibrinolytic activity (D-dimer level) in 8 cases each of a control (saline) group, a u-PA (30 kU/kg) group, a compound A (2.5 µg/kg) group, and a combination group of u-PA (30 kU/kg) and compound A (2.5 µg/kg).

(6) The comparison of the compound A (2.5 μg/kg) group or the t-PA (0.021 mg/kg) single administration group with the combination group was carried out by two-way ANOVA. As a result, synergistic fibrinolytic activity (D-dimer level) was confirmed in the combination group (FIG. 3).

(7) The dose of t-PA alone indicating fibrinolytic activity (D-dimer level) equivalent to the fibrinolytic activity (D-dimer level) of the combination group was inversely estimated by the linear regression of dose-response correlation using individual data on the control (saline) group and the t-PA (0.021, 0.042, and 0.083 mg/kg) groups. As a result, it was inversely estimated that the fibrinolytic activity (D-dimer level) of the combination group of compound A (2.5 μg/kg) and t-PA (0.021 mg/kg) corresponds to the fibrinolytic activity (D-dimer level) of t-PA (0.054 mg/kg (95% confidence interval: 0.049 to 0.058 mg/kg)).

These results suggested that the dose of the plasminogen activator necessary for exerting a fibrinolytic effect is reduced to 36% to 43% of the dose of single administration, by the combined use with compound A.

Example 2

Test on Combined Use with u-PA

1. Preparation of Administration Solution (1) u-PA (urokinase injection "Fuji" (registered trademark) 60,000, Wakamoto Co., Ltd.) was adjusted to 90 kU/mL with injectable water.

(2) Compound A was dissolved in saline to prepare a 1.0 mg/mL solution. The solution was further diluted to 0.0050 mg/mL using saline. The dose of compound A was indicated in terms of a free form (conversion factor: 0.6301).

(3) Appropriate amounts of saline, the 90 kU/mL u-PA solution, and the 0.0050 mg/mL compound A solution were mixed to respectively prepare administration solutions for a u-PA (30 kU/kg) group, a compound A (2.5 μg/kg) group, and a combination group of u-PA (30 kU/kg) and compound A (2.5 μg/kg).

(4) 5 mL of saline was added to 10 mL (standard) of a tissue factor (Dade (registered trademark) Innovin (registered trademark), Sysmex Corp.) to prepare a tissue factor solution.

2. Administration to Rat and Measurement of Fibrinolytic Activity (1) Eleven-week-old male Wistar rats (Japan SLC, Inc.) were fasted from a day before the experiment. On the basis of their body weights measured in the morning on the day of the experiment, 8 rats were assigned to each of 4 groups: a control (saline) group, a u-PA (30 kU/kg) group, a compound A (2.5 μg/kg) group, and a combination group of u-PA (30 kU/kg) and compound A (2.5 μg/kg).

(2) These rats were anesthetized by the administration of 100 mg/kg thiopental sodium (Ravonal (registered trademark), Mitsubishi Tanabe Pharma Corp.), and the tissue factor solution was continuously administered at 7.5 mL/kg/hr for 20 minutes from the jugular veins. 25 minutes after the start of the administration of the tissue factor, the administration solution for each group was rapidly administered from the jugular veins. 45 minutes after the start of the administration of the tissue factor, blood was collected from the jugular veins into syringes supplemented with citric acid in advance, and plasma was prepared by centrifugation. The plasma was diluted 20-fold using a factor diluent (LSI Medience Corp.). D-dimer levels were measured using LPIA-Ace D-D dimer II and ACL TOP 500 CTS (Instrumentation Laboratory) and used as an index for fibrinolytic activity (FIG. 4).

3. Statistical Analysis (1) Microsoft Excel 2010 and SAS System Release 9.2 were used in statistical analysis.

(2) For each group, the basic statistics (mean and standard error) of the D-dimer levels were calculated and used as results relating to fibrinolytic activity (Table 2).

TABLE 2

| Group | N | D-dimer level (μg/mL) | |
| --- | --- | --- | --- |
| | | Mean | Standard error |
| Control (saline) group | 8 | 24.2 | 5.2 |
| u-PA (30 kU/kg) group | 8 | 67.5 | 17.9 |
| Compound A (2.5 μg/kg) group | 8 | 103.8 | 17.0 |
| Combination group of u-PA (30 kU/kg) and compound A (2.5 μg/kg) | 8 | 214.0 | 8.5 |

(3) The comparison of the u-PA single administration group with the control group, the comparison of the compound A single administration group with the control group, and the comparison of the combination group with the control group were carried out by the Student's t test. The calculated P value was rounded off and indicated down to four decimal places, and the significance level was set to two-sided 5%.

As a result, the u-PA single administration group exhibited significantly excellent fibrinolytic activity (D-dimer level) with respect to the control group (P=0.0476). Also, the compound A single administration group exhibited significantly excellent fibrinolytic activity (D-dimer level) with respect to the control group (P=0.0019). Furthermore, the combination group exhibited significantly excellent fibrinolytic activity (D-dimer level) with respect to the control group (P<0.0001).

(4) The comparison of the u-PA single administration group with the combination group and the comparison of the compound A single administration group with the combination group were carried out by the parametric Dunnett's test. The calculated P value was rounded off and indicated down to four decimal places, and the significance level was set to two-sided 5%.

Figure 5:
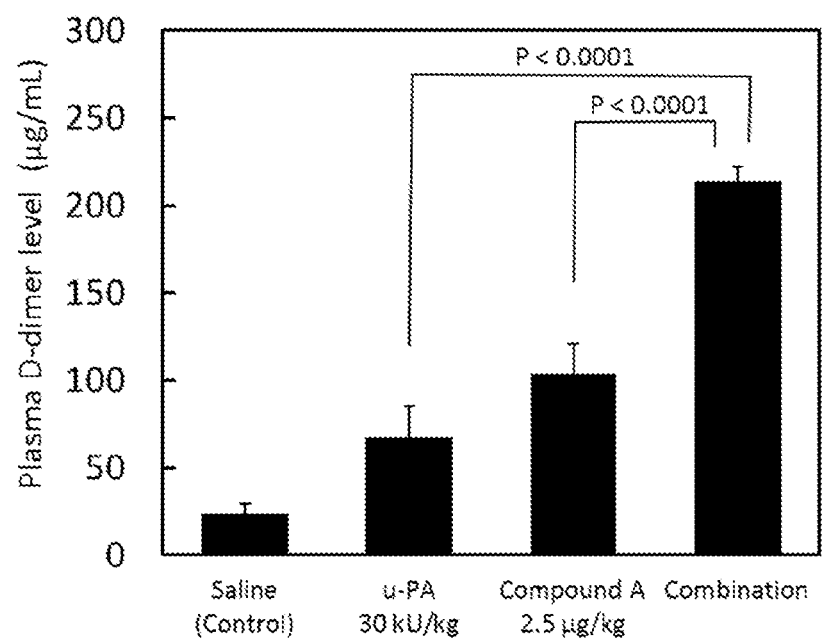
FIG. 5 is a diagram showing a mean (standard error) of fibrinolytic activity (D-dimer level) in 8 cases each of a control (saline) group, a u-PA (30 kU/kg) group, a compound A (2.5 µg/kg) group, and a combination group of u-PA (30 kU/kg) and compound A (2.5 µg/kg), and the comparison (P value) of the u-PA (30 kU/kg) and compound A (2.5 µg/kg) single administration groups with the combination group.

As a result, the combination group exhibited significantly excellent fibrinolytic activity (D-dimer level) with respect to the u-PA single administration group (P<0.0001). Also, the combination group exhibited significantly excellent fibrinolytic activity (D-dimer level) with respect to the compound A single administration group (P<0.0001) (FIG. 5).

Figure 6:
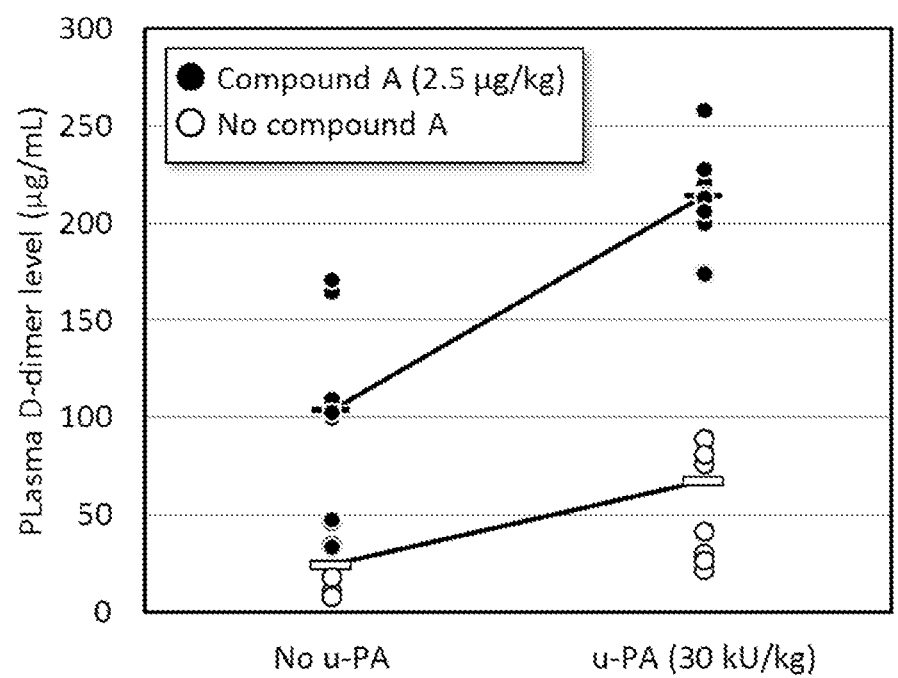
FIG. 6 is a diagram showing the comparison of the u-PA (30 kU/kg) and compound A (2.5 µg/kg) single administration groups with the combination group by two-way ANOVA. In the diagram, the plot depicts individual values, and the horizontal lines depict a mean of 8 cases each of the groups.

(5) The comparison among the u-PA single administration group, the compound A single administration group, and the combination group was carried out by two-way ANOVA. As a result, synergistic fibrinolytic activity (D-dimer level) was confirmed in the combination group (FIG. 6).

INDUSTRIAL APPLICABILITY

The present invention showed that the administration of a particular TAFIa inhibitor in combination with a plasminogen activator exhibits synergistic fibrinolytic activity. Thus, the pharmaceutical composition and the method of the present invention are useful in the treatment or prevention of thrombosis or embolism or a sequela thereof.

The invention claimed is:
1. A pharmaceutical composition for treatment or prevention of thrombosis or embolism or a sequela thereof, comprising a compound of formula (I):

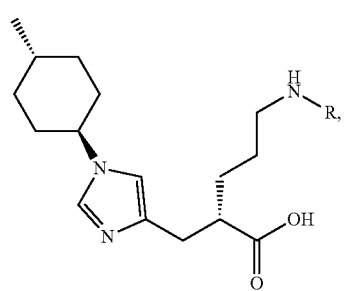

(I)

or a pharmacologically acceptable salt thereof, and
a plasminogen activator,
wherein R is a hydrogen atom, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a {1-[(cyclohexylcarbonyl)oxy]ethoxy}carbonyl group, or a (1-acetoxyethoxy)carbonyl group, and the pharmaceutical composition exhibits synergistic fibrinolytic activity.

2. The pharmaceutical composition of claim 1, wherein the compound of formula (I) or the pharmacologically acceptable salt thereof and the plasminogen activator are included in separate preparations.

3. The pharmaceutical composition of claim 1, wherein both the compound of formula (I) or the pharmacologically acceptable salt thereof and the plasminogen activator are included in a single preparation.

4. The pharmaceutical composition of claim 1, wherein the plasminogen activator is a tissue plasminogen activator (t-PA).

5. The pharmaceutical composition of claim 4, wherein the t-PA is alteplase.

6. The pharmaceutical composition of claim 1, wherein the plasminogen activator is urokinase (u-PA).

7. The pharmaceutical composition of claim 1, wherein R is a hydrogen atom.

8. The pharmaceutical composition of claim 7, wherein the pharmacologically acceptable salt is a p-toluenesulfonate.

9. The pharmaceutical composition of claim 1, wherein R is a [1-(isobutyryloxy)ethoxy]carbonyl group.

10. The pharmaceutical composition of claim 9, wherein R is a [(1R)-1-(isobutyryloxy)ethoxy]carbonyl group.

11. The pharmaceutical composition of claim 1, wherein the thrombosis or embolism is acute coronary syndrome; venous thromboembolism; thrombosis or embolism occurring in the cardiovascular system after a surgical operation; thrombosis or embolism after an artificial joint replacement operation; inflammation-related intravascular disease; peripheral vascular disorder-derived or -related disease; tumor-related disease; or organ disorder attributed to thrombus or embolus.

12. The pharmaceutical composition of claim 11, wherein the thrombosis or embolism is myocardial infarction, stable angina, or unstable angina; deep vein thrombosis or pulmonary embolism; thrombosis or embolism occurring in the cardiovascular system after vessel revascularization, angioplasty, stent placement, or bypass surgery; thrombosis or embolism after a knee joint replacement operation or hip joint replacement operation; intravascular disease related to sepsis or disseminated intravascular coagulation syndrome (DIC); disease derived from or related to peripheral arterial occlusion (PAO), arteriosclerosis, or diabetes mellitus; disease related to solid cancer or blood cancer; or organ disorder attributed to pulmonary embolus, cerebral infarction, or renal infarction.

13. The pharmaceutical composition of claim 1, wherein the thrombosis or embolism is disease caused by contact with foreign matter in the body; or disease caused by contact between blood and a medical device outside the body.

14. The pharmaceutical composition of claim 13, wherein the thrombosis or embolism is disease caused by contact with a medical device.

15. The pharmaceutical composition of claim 14, wherein the thrombosis or embolism is disease caused by contact with a joint prosthesis used in joint replacement, a vascular catheter, a vascular prosthesis, an intravascular stent, or a prosthetic valve.

16. The pharmaceutical composition of claim 13, wherein the thrombosis or embolism is disease caused by contact between blood and a pump oxygenator used in a cardiac operation or a medical device used in hemodialysis.

17. The pharmaceutical composition of claim 1, wherein the thrombosis or embolism is myocardial infarction, angina pectoris, acute coronary syndrome, cerebral infarction, deep vein thrombosis, pulmonary embolism, or peripheral arterial occlusion.

18. A method of treating or preventing thrombosis or embolism or a sequela thereof, comprising administering a compound of formula (I):

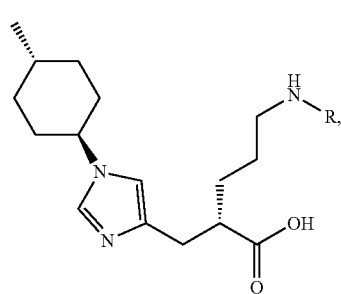

or a pharmacologically acceptable salt thereof, in combination with a plasminogen activator to a warm-blooded animal,
wherein R is a hydrogen atom, a [(5-methyl-2-oxo-1,3-dioxol-4-yl)methoxy]carbonyl group, a [1-(isobutyryloxy)ethoxy]carbonyl group, a [1-(2,2-dimethylpropanoyloxy)ethoxy]carbonyl group, a {1-[(cyclohexylcarbonyl)oxy]ethoxy}carbonyl group, or a (1-acetoxyethoxy)carbonyl group, and
the method exhibits synergistic fibrinolytic activity.

19. The method of claim 18, wherein the compound of formula (I) or the pharmacologically acceptable salt thereof and the plasminogen activator are included in separate preparations and are administered at the same time or different times.

20. The method of claim 18, wherein both the compound of formula (I) or the pharmacologically acceptable salt thereof and the plasminogen activator are included and administered in a single preparation.

21. The method of claim 18, wherein the plasminogen activator is a tissue plasminogen activator (t-PA).

22. The method of claim 21, wherein the t-PA is alteplase.

23. The method of claim 18, wherein the plasminogen activator is urokinase (u-PA).

24. The method of claim 18, wherein R is a hydrogen atom.

25. The method of claim 24, wherein the pharmacologically acceptable salt is a p-toluenesulfonate.

26. The method of claim 18, wherein R is a [1-(isobutyryloxy)ethoxy]carbonyl group.

27. The method of claim 26, wherein R is a [(1R)-1-(isobutyryloxy)ethoxy]carbonyl group.

28. The method of claim 18, wherein the thrombosis or embolism is acute coronary syndrome; venous thromboembolism; thrombosis or embolism occurring in the cardiovascular system after a surgical operation; thrombosis or embolism after an artificial joint replacement operation; inflammation-related intravascular disease; peripheral vascular disorder-derived or -related disease; tumor-related disease; or organ disorder attributed to thrombus or embolus.

29. The method of claim 28, wherein the thrombosis or embolism is myocardial infarction, stable angina, or unstable angina; deep vein thrombosis or pulmonary embolism; thrombosis or embolism occurring in the cardiovascular system after vessel revascularization, angioplasty, stent placement, or bypass surgery; thrombosis or embolism after a knee joint replacement operation or hip joint replacement operation; intravascular disease related to sepsis or disseminated intravascular coagulation syndrome (DIC); disease derived from or related to peripheral arterial occlusion (PAO), arteriosclerosis, or diabetes mellitus; disease related to solid cancer or blood cancer; or organ disorder attributed to pulmonary embolus, cerebral infarction, or renal infarction.

30. The method of claim 18, wherein the thrombosis or embolism is disease caused by contact with foreign matter in the body; or disease caused by contact between blood and a medical device outside the body.

31. The method of claim 30, wherein the thrombosis or embolism is disease caused by contact with a medical device.

32. The method of claim 31, wherein the thrombosis or embolism is disease caused by contact with a joint prosthesis used in joint replacement, a vascular catheter, a vascular prosthesis, an intravascular stent, or a prosthetic valve.

33. The method of claim 30, wherein the thrombosis or embolism is disease caused by contact between blood and a pump oxygenator used in a cardiac operation or a medical device used in hemodialysis.

34. The method of claim 18, wherein the thrombosis or embolism is myocardial infarction, angina pectoris, acute coronary syndrome, cerebral infarction, deep vein thrombosis, pulmonary embolism, or peripheral arterial occlusion.

35. The method of claim 18, wherein the warm-blooded animal is a human.

* * * * *